United States Patent [19]
Rupp et al.

[11] Patent Number: 5,653,691
[45] Date of Patent: Aug. 5, 1997

[54] THICKENED INNER LUMEN FOR UNIFORM STENT EXPANSION AND METHOD OF MAKING

[76] Inventors: Garry Eugene Rupp, 10777-B Andrea Ter., Santee, Calif. 92071; Randell L. Werneth, 11315 Affinity Ct., #145, San Diego, Calif. 92131; Perfecta P. Tilos, 8277 Calle Pino, San Diego, Calif. 92126

[21] Appl. No.: 637,959

[22] Filed: Apr. 25, 1996

[51] Int. Cl.⁶ .................................................. A61M 29/00
[52] U.S. Cl. ............................................... 604/96; 606/194
[58] Field of Search .................... 604/96, 103, 171, 604/280, 282, 273, 104; 128/658; 606/192, 194, 195, 108

[56] References Cited

U.S. PATENT DOCUMENTS

| | | | |
|---|---|---|---|
| 4,886,062 | 12/1989 | Wiktor | 128/343 |
| 4,981,478 | 1/1991 | Evard et al. | 604/282 |
| 5,133,732 | 7/1992 | Wiktor | 606/195 |
| 5,256,143 | 10/1993 | Miller et al. | 604/96 |
| 5,403,341 | 4/1995 | Solar | 606/198 |
| 5,409,495 | 4/1995 | Osborn | 606/108 |

FOREIGN PATENT DOCUMENTS

0553960  4/1993  European Pat. Off. .......... A61F 2/06

*Primary Examiner*—Corrine M. McDermott
*Assistant Examiner*—Cris L. Rodriguez
*Attorney, Agent, or Firm*—Dianne M. F. Plunkett; Harold R. Patton

[57] ABSTRACT

An intravascular catheter system for implanting a radially expandable stent within a body vessel including a catheter comprising an inner lumen tube, an inflation lumen tube, an inflatable balloon and at least one free standing built-up layer affixed to the outer diameter of the inner lumen tube, the built-up layer being internal to the balloon. A stent is mounted coaxially upon the balloon, the built-up layer extends coaxially within the stent but does not extend beyond the proximal and distal ends of the stent. The built-up layer is sufficiently thick as to cause the balloon to expand evenly and the stent to deploy uniformly. The method of manufacturing the built-up layer includes forming the layer from shrink wrap tubing or alternatively forming the layer from molded ultraviolet light curing adhesive.

17 Claims, 5 Drawing Sheets

PRIOR ART

THICKENED INNER LUMEN FOR UNIFORM STENT EXPANSION AND METHOD OF MAKING

FIELD OF THE INVENTION

The present invention relates to an intravascular stent deployment system and method of manufacture and more particularly to a balloon catheter for stent delivery with the catheter inner lumen tube having a greater outer diameter for a central portion of the area covered by the stent thereby permitting more uniform expansion of the stent.

BACKGROUND OF THE INVENTION

Percutaneous transluminal coronary angioplasty (PTCA) is used to reduce arterial build-up of cholesterol fats or atherosclerotic plaque. Typically a first guidewire of about 0.038 inches in diameter is steered through the vascular system to the site of therapy. A guiding catheter, for example, can then be advanced over the first guidewire. The first guidewire is then removed. A balloon catheter on a smaller 0.014 inch diameter guidewire is advanced within the guiding catheter to a point just proximal to the stenosis. The second guidewire is advanced into the stenosis, followed by the balloon at the distal end of the catheter. The balloon is then inflated causing the site of the stenosis to compress into the arterial wall. The dilatation of the occlusion, however, can form flaps, fissures and dissections which threaten re-closure of the dilated vessel or even perforations in the vessel wall. Implantation of a metal stent can provide support for such flaps and dissections and thereby prevent reclosure of the vessel or provide a patch repair for a perforated vessel wall until corrective surgery can be performed. Reducing the possibility of restenosis after angioplasty reduces the likelihood that a secondary angioplasty procedure or a surgical bypass operation will be necessary.

An implanted prosthesis such as a stent can preclude additional procedures and maintain vascular patency by mechanically supporting dilated vessels to prevent vessel collapse. Stents can also be used to repair aneurysms, to support artificial vessels as liners of vessels or to repair dissections. Stents are suited to the treatment of any body lumen, including the vas deferens, ducts of the gallbladder, prostate gland, trachea, bronchus and liver. The body lumens range in size from the small coronary vessels to the 28 mm aortic vessel. The invention applies to acute and chronic closure or reclosure of body lumens.

A typical stent is a cylindrically shaped wire formed device intended to act as a permanent prosthesis. A stent is deployed in a body lumen from a radially compressed configuration into a radially expanded configuration which allows it to contact and support a body lumen. The stent can be made to be radially self-expanding or expandable by the use of an expansion device. The self expanding stent is made from a resilient springy material while the device expandable stent is made from a material which is plastically deformable. A plastically deformable stent can be implanted during a single angioplasty procedure by using a balloon catheter bearing a stent which has been crimped onto the balloon. Stents radially expand as the balloon is inflated, forcing the stent into contact with the body lumen thereby forming a supporting relationship with the vessel walls.

The biocompatable metal stent props open blocked coronary arteries, keeping them from reclosing after balloon angioplasty. A balloon of appropriate size and pressure is first used to open the lesion. The process is repeated with a stent crimped on a balloon. The stent is deployed when the balloon is inflated. The stent remains as a permanent scaffold after the balloon is withdrawn.

U.S. Pat. No. 4,886,062 to Wiktor for "Intravascular Radially Expandable Stent and Method of Implant" discloses a two-dimensional zig-zag form, typically a sinusoidal form.

U.S. Pat. No. 5,409,495 to Osborn for "Apparatus for Uniformly Implanting a Stent" discloses elastic restraining bands which exert a force at the proximal and distal ends of the balloon equal and opposite to that generated by the combined resistance of the sleeve and the stent tending to deform the balloon. In this way, the uneven expansion (end effects) are limited when the balloon is expanded which, in turn, inhibits a "dog boning" deformation at the proximal and distal regions of the balloon. FIGS. 3–6 show a balloon of complex manufacture.

As stent metal mass increases in stents having elements that can expand independently in the longitudinal direction, there is a tendency towards longitudinal compression at the center of the stent when expanded. The increased metal mass creates more radial hoop strength which in turn increases the mount of force required to expand the stent. The center of the stent has more radial hoop strength than the ends of the stent. As a result, the balloon expands first at the distal and proximal ends before expanding at the center. This creates a dumbbell shaped balloon. With the stent ends expanding first, the stent slides down the expanded balloon ends toward the center of the balloon which is as yet unexpanded because of the stent's greater radial hoop strength in the center. When the balloon ends have expanded completely, the stent has been compressed to approximately one-half of its original crimped length. Because the stent is compressed toward the center of the balloon, complete balloon expansion may not be possible. What is needed is a method of stent deployment which results in uniform stent expansion.

SUMMARY OF THE INVENTION

It is an object of the invention to provide a means for stent deployment which reduces longitudinal stent slippage during stent expansion and permits uniform radial stent expansion. A further object of the invention is to provide a method of molding parts which reduces costs, reduces the possibility of damage and produces a precision part. The present invention is accomplished by providing an intravascular catheter system for implanting a radially expandable stent within a body vessel including a catheter comprising an inner lumen tube, an inflation lumen tube, an inflatable balloon and at least one free standing built-up layer affixed to the outer diameter of the inner lumen tube, the built-up layer being internal to the balloon. A stent is mounted coaxially upon the balloon, the built-up layer extends coaxially within the stent but does not extend beyond the proximal and distal ends of the stent. The built-up layer is sufficiently thick as to cause the balloon to expand evenly and the stent to deploy uniformly. The method of manufacturing the built-up layer includes forming the layer from shrink wrap tubing or alternatively forming the layer from molded ultraviolet light curing adhesive.

DETAILED DESCRIPTION OF THE PREFERRED EMBODIMENTS

Figure 18:
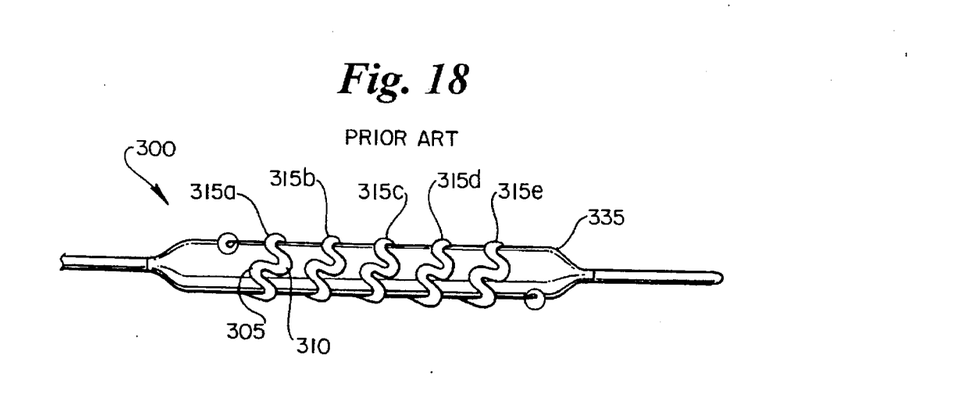
FIG. 18 is a side elevation overall view of a Wiktor stent fitted over a deflated balloon.

A typical Wiktor coronary stent is described in U.S. Pat. No. 4,886,062 herein incorporated by reference. Refer to FIG. 18 showing a side elevation overall view of a Wiktor stent 300 fitted over a deflated balloon 335. The Wiktor stent 300 is formed with a wire which is formed into zig-zags such as a sinusoidal wave form helix pattern the length of the stent by a means such as passing the wire through gears such as those disclosed in U.S. Pat. No. 2,153,936 issued to Owens et al. The zig-zags are formed by alternate peaks 305 and valleys 310. The zig-zags are canted toward the proximal and distal ends of the stent 300. The zig-zags form a plurality of spaced-apart elements 315a–e each extending 360 degrees around the hollow cylinder. Each of the elements 315a–e has a plurality of extendible portions such as the zig-zags which permit the wire elements 315a–e to be expanded from an unexpanded diameter to a second, expanded diameter.

A wire having formed zig-zags is wound around a forming mandrel to create the cylindrical stent shape. After the stent has been reduced to the objective outer diameter by compressing it on successively smaller mandrels, the proximal and distal ends of the wire segment are attached. The means of attachment may include looping the end segments together, twisting, biocompatible adhesive, brazing, welding or stamping.

The stent wire can have a diameter of about 0.001 inches to about 0.015 inches. A round wire is shown in the phantom stent 100 in FIG. 1. The balloon expandable stent can be made of an inert, biocompatible material with high corrosion resistance that can be plastically deformed at low-moderate stress levels such as tantalum, the preferred embodiment. Other acceptable materials include stainless steel, titanium ASTM F63-83 Grade 1, niobium or high carat gold K 19–22. A self-expanding device can be made by the use of superelastic nickel titanium (NiTi) such as Nitinol manufactured by Raychem or Forukawa.

The preferred form of the sinusoidal wave of the stent wire is a length of about 0.150 inches to about 0.090 inches and a wave amplitude of between about 0.050 inches and about 0.080 inches. Any wave length and amplitude combination that would provide adequate vessel hoop strength and vessel coverage is appropriate. The stent of this invention and balloon can be transported via a standard #7 French guiding catheter of 0.092 inches (2.3 mm) outer diameter or 8 French guiding catheter of 0.105 inches (2.7 mm) outer diameter. Once on location, the stent can be expanded radially by the expansion of the balloon 35; a ratio of 2.75:1 can be achieved with a wire diameter of approximately 0.005 inches and an initial stent diameter of 0.060 approximately inches.

As seen in FIG. 18, the stent 300 is centrally located and positioned with respect to the length of balloon 335. The stent 300 turns are evenly spaced so that when the stent 300 is expanded the stent 300 will provide even support inside the vessel and resist external loading. The stent 300 must expand evenly and permit the balloon 335 to expand evenly.

The Wiktor stent is formed of a hollow cylindrical wire winding having a plurality of spaced-apart circumferential elements 315a –e. Each element 315a–e extends 360 degrees around the hollow cylinder such that the elements 315a–e can move longitudinally as the stent 300 is expanded. Each of the elements 315a–e has a plurality of extendible portions 305, 310 which permit the wire elements 315a–e to be expanded. Each peak 305 and valley 310 pair comprises a wave. To achieve greater coverage, metal mass can be increased in a sinusoidal wave form stent 300 by having more waves per revolution, as for example, increasing from four waves to six waves. Stents such as that shown in FIG. 18 having elements 315a–e can expand independently in the longitudinal direction and can present special problems not presented by stents formed of a solid cylinder. As stent metal mass increases there is a tendency towards longitudinal compression at the center of the stent when expanded. The increased metal mass creates more radial hoop strength which in turn increases the amount of force required to expand the stent 300. The center of the stent has more radial hoop strength than the ends of the stent 300. The balloon expands first at the distal and proximal ends before expanding the center which is covered by the stem. This creates a dumbbell shaped balloon. With the stent ends expanding first, the stent slides down the expanded balloon ends toward the center of the balloon which is as yet unexpanded because of the stent's increased radial hoop strength in the center. As the proximal and distal ends of the balloon expand to approximately two-thirds of normal expansion diameter, the mid-section of the balloon begins to expand. When the balloon ends have expanded completely, the stent may have been compressed to approximately one-half of its original crimped length. Because the stent is compressed toward the center of the balloon, complete balloon expansion may not be possible.

Figure 1:
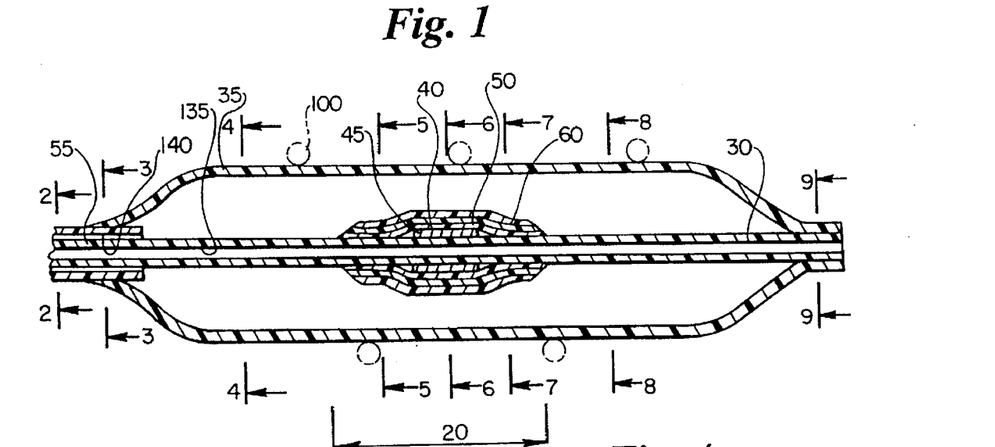
FIG. 1 is a longitudinal cross-section of a stent on a deployment device having multiple built-up layers according to the invention.
Figure 2:
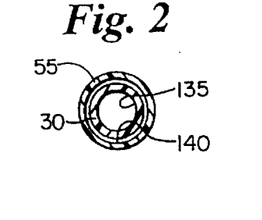
FIG. 2 is a cross-section along the lines 2—2 of FIG. 1.
Figure 3:
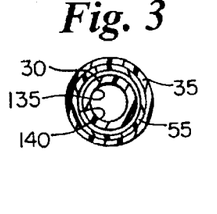
FIG. 3 is a cross-section along the lines 3—3 of FIG. 1.
Figure 4:
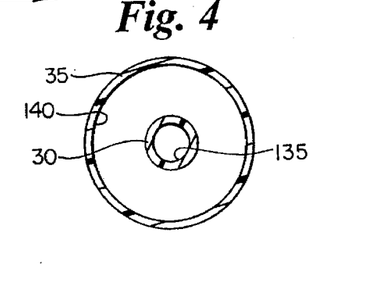
FIG. 4 is a cross-section along the lines 4—4 of FIG. 1.
Figure 5:
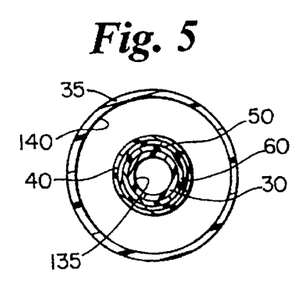
FIG. 5 is a cross-section along the lines 5—5 of FIG. 1.
Figure 6:
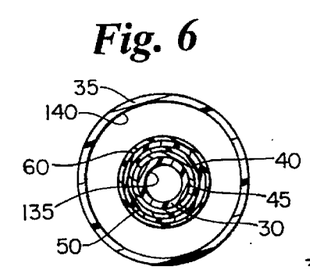
FIG. 6 is a cross-section along the lines 6—6 of FIG. 1.
Figure 7:
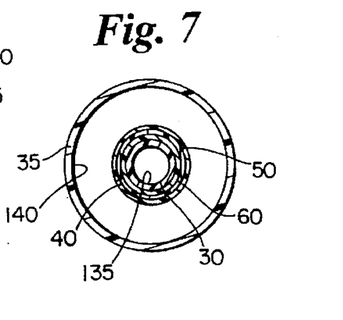
FIG. 7 is a cross-section along the lines 7—7 of FIG. 1.
Figure 8:
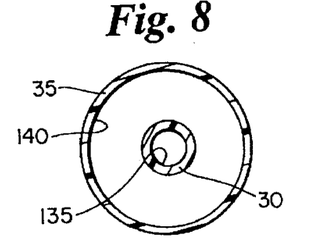
FIG. 8 is a cross-section along the lines 8—8 of FIG. 1.
Figure 9:
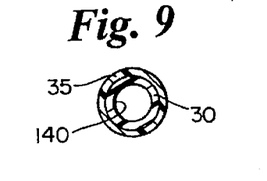
FIG. 9 is a cross-section along the lines 9—9 of FIG. 1.
Figure 16:
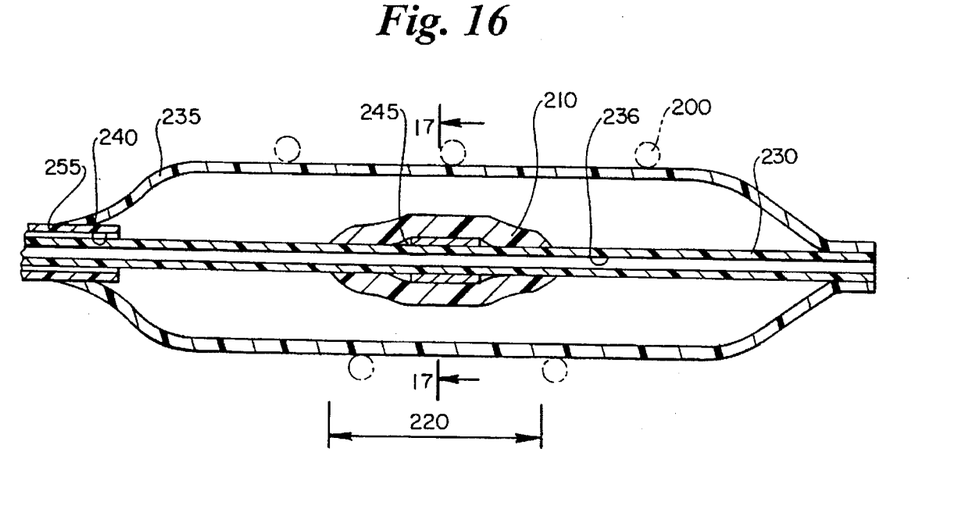
FIG. 16 is a longitudinal cross-section of a stent on a deployment device having a molded built-up layer according to the invention.

To prevent the dumbbell effect, a section of inner lumen tubing under the area of the stent can be built up as seen in FIGS. 1, or 16. Refer to FIG. 1. Since the portion of the stent 100 situated over the built up section 20 is already partially expanded, the center of the stent 100 will begin to expand to its full diameter at the same time as the balloon 35 ends begin to expand. The built up section 20 in the central portion of the stent 100 improves stent expansion by reducing radial hoop strength at the center of the stent 100 and also by giving this area of the stem 100 a head start on expansion so as to have the effect of pre-dilating the central portion of the stent.

The length of the built up section 20 varies with the length of the stent 100 being deployed. Stents can range from 0.197 inches (5 mm) to 1.97 inches (50 mm) in length. The preferred length of the built up section 20 is equal to one-third of the length of the stent 100. The built up section 20 should be centered between the proximal and distal ends of stent 100. The built up section 20 has a tapering profile at either end to direct the stent elements slightly away from the center of the stent as the stent starts to expand. In particular, the taper would cause the zig-zags to be canted slightly toward the ends to give them that initial direction as the stent begins to expand.

A typical catheter has inner lumen tubing 30 which may be made of High Density Polyethylene (HDPE) or polyamide. The inner lumen tubing 30 defines an inner lumen 135 which provides a passageway for a guidewire. The inner lumen tubing 30 may be either coaxial or biaxial with the inflation lumen tubing 55. The inflation lumen tubing 55 defines an inflation lumen 140. In FIG. 1, the inner lumen tubing 30 is coaxial with the inflation lumen tubing 55 and runs longitudinally therethrough. The inflation lumen may be made from polyimide, polyamide, polyester, Low Density Polyethylene (LDPE) or a jacketed spring coil. The distal end of the balloon 35 may be sealed to the distal end of the inner lumen tubing 30. The proximal end of the balloon 35 may be sealed to the distal end of the inflation lumen tubing 55. The balloon may be made from LDPE, Linear Low Density Polyethylene (LLDPE), polyethylene terephthalate (PET) or Nylon. One metal marker band 45, in FIG. 10 or two metal marker bands 65, or more than 2 metal marker bands may be positioned within the balloon on the outer surface of the inner lumen tubing FIG. 1 #30, FIG. 10 #130, FIG. 16 #230 to enable the physician to observe the advancement of the balloon under fluoroscopy.

A typical guidewire is 0.014 inches. The inner diameter of the inner lumen tubing 30, 130, 230 is typically 0.017 inches to allow approximately 0.003 inches for clearance. The outer diameter of the inner lumen tubing 30, 130, 230 is typically 0.021 inches.

When a stent 100 is crimped upon a balloon 35, the plastic balloon is compressed between two pieces of metal, the marker band 45 and the stent 100. This could cause pin hole leaks if not properly crimped. To avoid such leaks and provide a built up section 20 of sufficient thickness to avoid the dumbbell effect, one or more free standing built-up layers can be affixed to the inner lumen tubing 30, 130, 230. FIGS. 1–9 show 3 such built-up layers, 40, 50 and 60.

The total increase in thickness of all the built-up layers within the outer diameter of the inner lumen tubing 30, 130, 230 over the built up section 20, 120, 220 can range from about 0.001 inches to about 0.060 inches at its thickest point. The built up section 20, 120, 220 proximal and distal ends taper down. The thickness of each individual built-up layer ranges between approximately 0.001 inches and 0.010 inches and should more preferably should range from about 0.002 inches to about 0.008 inches in thickness, but not less than about 0.002 inches in thickness. If a built-up layer is too thin it may puncture when crimped between the stent and marker band in addition to insufficiently building up the section to uniformly deploy the stent. If the built up section 20 becomes too thick, the distal end of the catheter will become too stiff and will fail to track properly within tortuous vessels. The most preferable thickness of a single built-up layer is about 0.003 inches. When shaft stock tubing is heat shrunk about the built up section 20, the typical thickness of an individual layer ranges between 0.003 to 0.004 inches. Each built-up layer 40, 50, 60 can be made from polyethylene or nylon or other suitable biocompatable materials.

The inner lumen tubing 30 can be built up by adding built-up layers 40, 50, 60 of a polymer material or by molding. To build up the inner lumen tubing 30 by adding one or more layers of a polymer material such as polyethylene (PE) as seen in FIG. 1, one can heat shrink layers of PE onto the inner lumen tubing 30. This can be accomplished by using a hot air torch box or a heat lamp from about 230 degrees to about 300 degrees for about 5 to about 60 seconds. One layer of thick material or several layers of thinner material can be used to achieve the desired increase in diameter. Multiple layers may be more flexible then a single larger layer. The proximal and distal ends of the PE material are then shaved and tapered to form a smooth transition edge. The preferred number of built-up layers is not more than 3 because of the amount of time each layer adds to manufacturing; for each layer, a shrink wrap tube will have to be cut to length, shrunk and shaved.

Using shrink wrap tubing or any other material which requires heat in the process can cause damage to the inner lumen tubing 30. Shrinkable tubing also may have variability in tubing wall thickness and would pass that variability into the product. With shrinkable tubing, tapering would have to be performed, as for example, manually. This adds the potential for damage as well as the additional costs of manufacture. The assembly steps associated with shrink wrap tubing are labor intensive.

Figure 10:
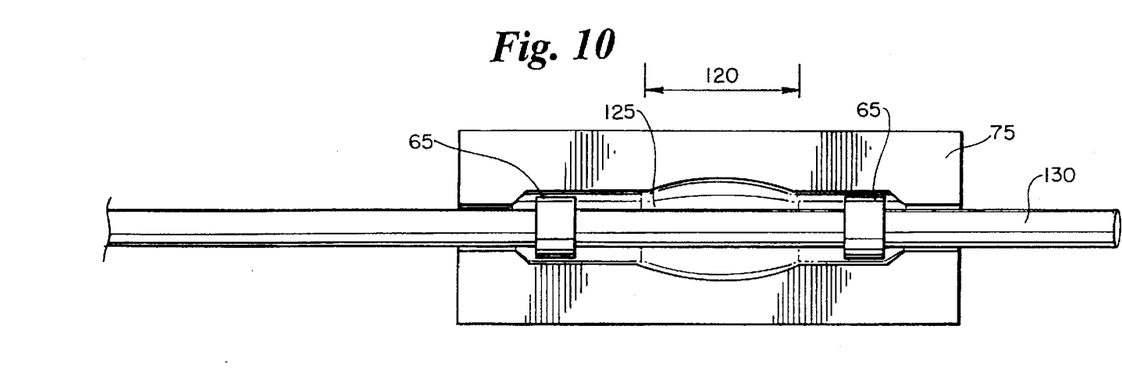
FIG. 10 is a longitudinal cross-sectional view of a mold containing inner lumen tubing having marker bands affixed.

Refer to FIG. 10. Molding is an alternative to the use of shrink wrap tubing to build up a section 120 of the inner lumen tubing 130. Molding can be done with silicon parts but the tooling costs for producing such a mold can be high. Applicant uses instead a cast-in-place flexible adhesive which is formed by dispensing a flexible adhesive into a mold. After the adhesive is dispensed, the adhesive is cured.

Figure 11:
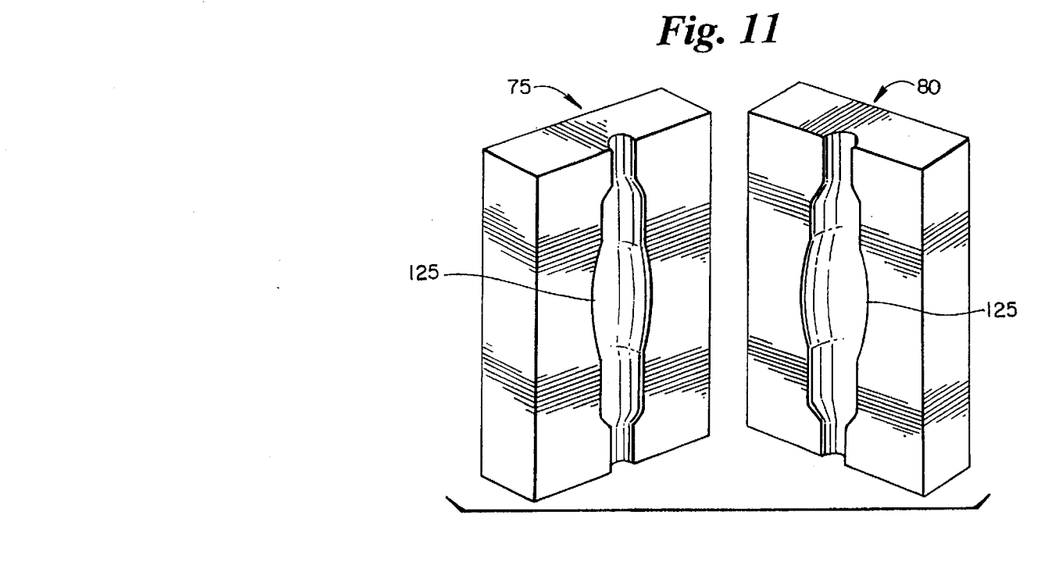
FIG. 11 is a perspective view of a pair of molds of FIG. 10.
Figure 12:
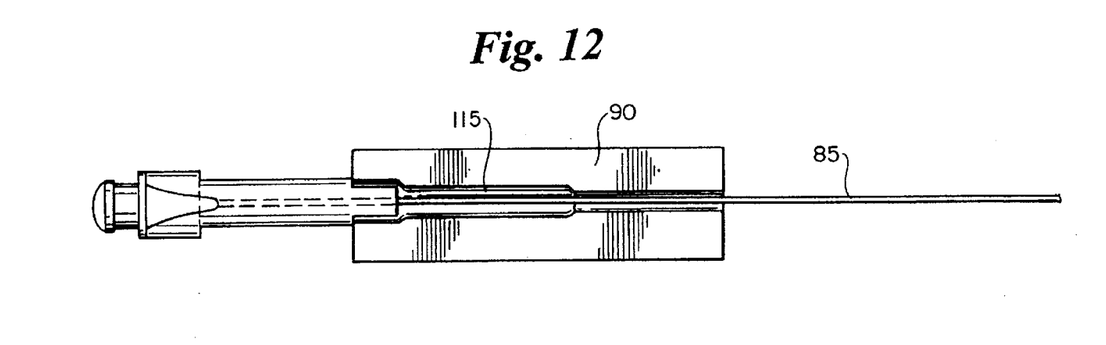
FIG. 12 is a longitudinal cross-sectional view of a mold for a catheter strain relief with the catheter therein.
Figure 13:
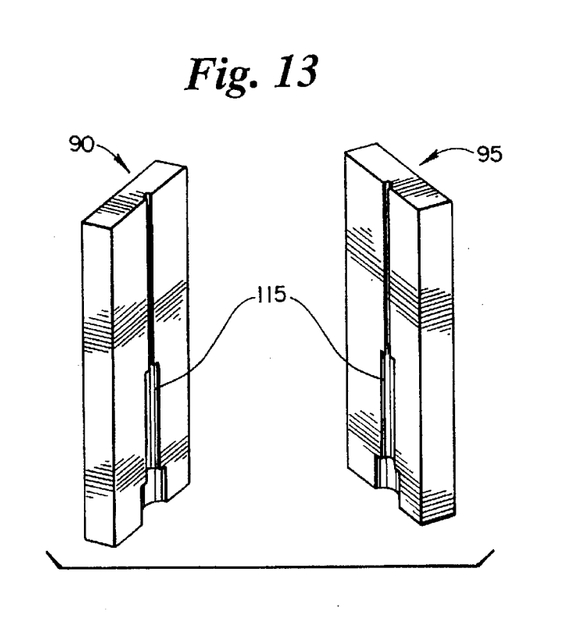
FIG. 13 is a perspective view of a pair of molds of FIG. 12.
Figure 14:
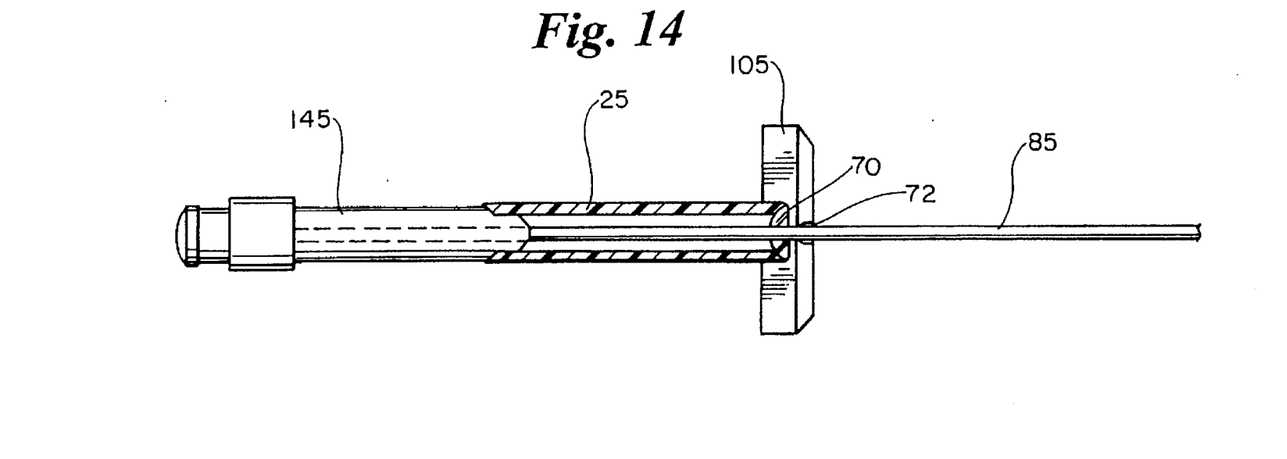
FIG. 14 is a longitudinal cross-sectional view of the catheter and alternative mold to FIG. 12 including a mold alignment fixture.
Figure 15:
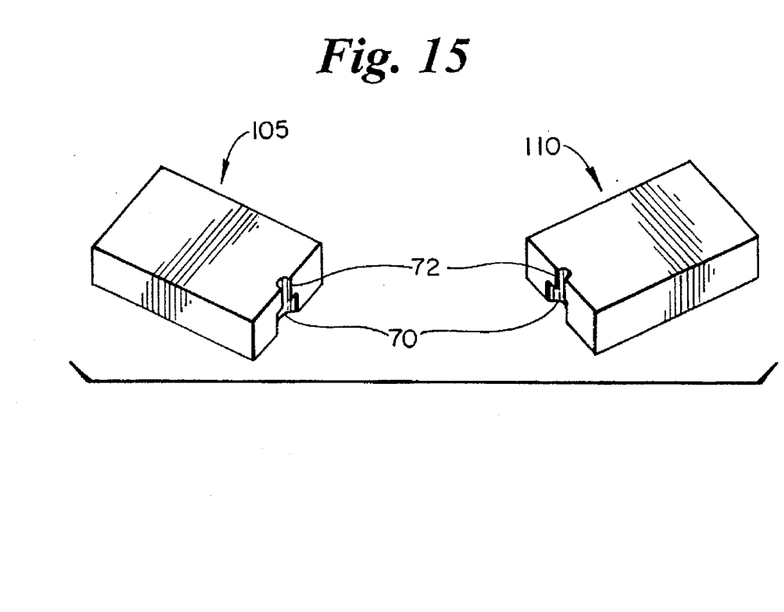
FIG. 15 is a perspective view of a pair of mold alignment fixtures of FIG. 14.

The advantage of a cast-in-place adhesive part is that it maintains an accurate and precise profile which does not need to be shaved. Less labor is involved in the molding process. The part is adhered to the catheter body at the same time the part is cast and cured. The resulting assembly forms a bond between the catheter body and the part. Cast-in-place adhesive parts are applicable to any assembly which may require two components to be bonded together as for example, strain relief parts or an inner lumen tubing built-up layer. Molds 75, 80 used for building up the inner lumen tubing 130 are seen in FIGS. 10 and 11. Molds 90, 95 for creating a strain relief are seen in FIGS. 12 and 13. An alternative to strain relief molds 90, 95 is seen in FIG. 14. In FIG. 14 the adhesive is dispensed into molding tubing 25 in order to fashion the strain relief. The related mold alignment fixtures 105, 110 are seen in FIGS. 14 and 15.

The molds 75, 80, 90, 95, 25 which are used for cast-in-place adhesive parts should be made of, or lined/coated with a material which will not adhere to the flexible adhesive. Suitable materials for the mold/liner include silicone and polyurethane. A fluoropolymer such as TEFLON™ from E. I. Du Pont de Nemours & Company, Wilmington, Del. could also be used among others. If an ultraviolet light cured adhesive is used, the mold must be transparent. Suitable materials for transparent molds include polycarbonate or acrylic.

Figure 17:
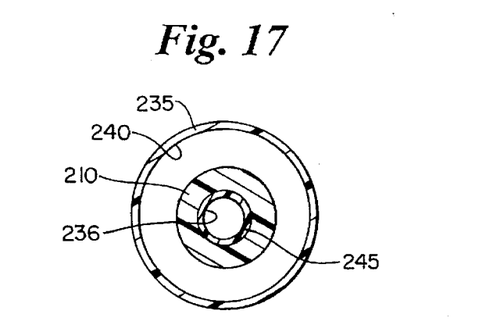
FIG. 17 is a cross-section along the lines 17—17 of FIG. 16.

Refer to FIGS. 16 and 17. To create a molded built up section 220 the following procedure may be employed. The inner lumen tubing 230 is placed in the build up cavity 125 of the inner lumen tubing mold side one 75. The inner lumen tubing mold side two 80 seen in FIG. 11 is then closed. Suitable flexible adhesive is injected into the built up cavity 125 and cured. The resulting adhesive built-up layer 210 forms a built up section 220 is shown in FIG. 16. Once the inner lumen tubing 230 is built up, the distal end of the balloon 235 is attached to the distal end of the inner lumen tubing 230 and the proximal end of the balloon 235 is attached to the distal end of the inflation lumen tubing 255 as seen in FIG. 16. The inner lumen tubing 230 defines the inner lumen 236. After the balloon 235 is wrapped and heat set, the stent 200 is crimped down onto the balloon 235. The adhesive built-up layer 210 keeps the balloon 235 from becoming punctured between the metal stent 200 and the metal marker band 245. The built up section 220 causes the middle of the stent 200 to be slightly expanded, thus reducing the radial hoop strength and reducing the amount of force required to expand the middle of the stent 200. This allows the stent 200 to be expanded uniformly simultaneously.

To mold a strain relief, refer to FIG. 12. A catheter shaft 85 is placed in the strain relief cavity 115 of the strain relief mold side one 90. The strain relief mold side two 95 seen in FIG. 13 is then closed. A strain relief can also be formed with a section of molding tubing 25 and an alignment fixture 105, 110 as seen in FIGS. 14 and 15. Use of an alignment fixture 105, 110 results in the proper centering of the catheter shaft 85 within the molding tubing 25. The alignment fixture 105 when placed next to its mirror image counterpart 110, forms a passage therethrough. The passage has a larger aperture 70 at the proximal end than the aperture at the distal end 72. The apertures are sized to fit the particular catheter manifold 145. Flexible adhesive is then injected into either the molding tubing 25 or the strain relief cavity 115 and cured. The assembly is removed from mold 25 or molds 90/95 and further processed.

Ultraviolet (UV) light curing adhesives are preferable because heat which may damage the catheter is not required. Furthermore, minimal curing time, generally under 20 seconds are required. A suitable light source is required for UV curing adhesives. The preferred material for UV/Light curing adhesive includes 1-20270 Dymax ® Ultra Light Weld™ from Dymax Corp. of Torrington Conn. Loctite ® manufactured by Loctite Corp. in Hartford Conn. could also be used. UV/light cured adhesives are superior to room temperature curing adhesives which take longer.

The preceding specific embodiments are illustrative of the practice of the invention. It is to be understood, however, that other expedients known to those skilled in the art or disclosed herein, may be employed without departing the scope of the appended claims.

| No. | Component |
| --- | --- |
| 20 | Built Up Section |
| 25 | Molding Tubing |
| 30 | Inner Lumen Tubing |
| 35 | Balloon |
| 40 | First Built-up Layer |
| 45 | Marker Band |
| 50 | Second Built-up Layer |
| 55 | Inflation Lumen Tubing |
| 60 | Third Built-up Layer |
| 65 | Marker Band Pair |
| 70 | Molding Tubing Proximal Aperture |
| 72 | Molding Tubing Distal Aperture |
| 75 | Inner Lumen Tubing Mold Side One |
| 80 | Inner Lumen Tubing Mode Side Two |
| 85 | Catheter Shaft |
| 90 | Strain Relief Mold Side One |
| 95 | Strain Relief Mode Side Two |
| 100 | Stent |

-continued

| No. | Component |
| --- | --- |
| 105 | Mold Alignment Fixture Side One |
| 110 | Mold Alignment Fixture Side Two |
| 115 | Strain Relief Cavity |
| 120 | Built Up Section |
| 125 | Built Up Cavity |
| 130 | Inner Lumen Tubing |
| 135 | Inner Lumen |
| 140 | Inflation Lumen |
| 145 | Manifold |
| 200 | Stent |
| 210 | Adhesive Built-up Layer |
| 220 | Built Up Section |
| 230 | Inner Lumen Tubing |
| 235 | Balloon |
| 236 | Inner Lumen |
| 240 | Inflation Lumen |
| 245 | Marker Bank |
| 255 | Inflation Lumen Tubing |
| 300 | Wiktor Stent |
| 305 | Peak |
| 310 | Valley |
| 315a-e | Elements |
| 335 | Balloon | what is claimed is:

1. An intravascular catheter system for implanting a radially expandable stent within a body vessel the combination comprising:
    a catheter comprising:
        an inner lumen tube defining an inner lumen, the inner lumen tube having a proximal end, a distal end and an outer diameter;
        an inflation lumen tube defining an inflation lumen, the inflation lumen tube having a proximal end and a distal end, the inner lumen tube extending distal to the inflation lumen tube;
        an inflatable balloon having a proximal end and a distal end, the balloon distal end being sealingly affixed to the distal end of the inner lumen tube, the balloon proximal end being sealingly affixed to the distal end of the inflation lumen tube, the balloon being in fluid communication with the inflation lumen; and
        at least one free standing built-up layer affixed to the outer diameter of the inner lumen tube, the built-up layer being internal to the balloon, the built-up layer having proximal and distal ends;
    a stent having a proximal end and a distal end, the stent mounted coaxially upon the balloon, the built-up layer extending coaxially within the stent, the built-up layer not extending beyond the proximal and distal ends of the stent and with the built-up layer being sufficiently thick as to cause the balloon to expand evenly and the stent to deploy uniformly.

2. A catheter system according to claim 1 wherein the length of the built-up layer is approximately one-third of the length of the stent.

3. A catheter system according to claim 1 wherein the built-up layer is formed of at least one heat shrunk layer.

4. A catheter system according to claim 1 wherein the built-up layer is formed from molded adhesive.

5. A catheter system according to claim 4 wherein the adhesive is an Ultraviolet light cured adhesive.

6. A catheter system according to claim 1 wherein the built-up layer ranges between 0.001 inches and 0.060 inches in thickness at its thickest point, the thickest point being central to the stent.

7. A catheter system according to claim 1 wherein the inner lumen tube is coaxial with and extends longitudinally within the inflation lumen tube.

8. A catheter system according to claim 1 wherein the stent is formed of a hollow cylindrical wire winding having a plurality of spaced-apart circumferential elements, each element extending 360 degrees around the hollow cylinder such that the elements can move longitudinally as the stent is expanded, each of the elements having a plurality of extendible portions which permit the wire elements to be expanded from an unexpanded diameter to a second, expanded diameter.

9. A catheter system according to claim 8 wherein the stent is formed of a helically wound wire having longitudinally movable elements.

10. A catheter system according to claim 1 wherein the stent has a centrally raised portion as it is mounted on a deflated balloon.

11. A catheter system according to claim 1 wherein the built-up layer tapers downward toward the proximal and distal ends.

12. A catheter system according to claim 1 wherein the stent is formed of a wire wound into a zig-zag pattern canted toward the proximal and distal ends of the stent.

13. An intravascular catheter system for implanting a radially expandable stent within a body vessel the combination comprising:

a catheter comprising:
- an inner lumen tube defining an inner lumen, the inner lumen tube having a proximal end, a distal end and an outer diameter;
- an inflation lumen tube defining an inflation lumen, the inflation lumen tube having a proximal end and a distal end, the inner lumen tube extending distal to the inflation lumen tube;
- an inflatable balloon having a proximal end and a distal end, the balloon distal end being sealingly affixed to the distal end of the inner lumen tube, the balloon proximal end being sealingly affixed to the distal end of the inflation lumen tube, the balloon being in fluid communication with the inflation lumen tube;
- at least one marker band being affixed to the inner lumen tube within the balloon such that the marker band can be viewed under fluoroscopy;
- at least one free standing built-up layer affixed to the outer diameter of the inner lumen tube, the built-up layer being internal to the balloon, the built-up layer extending at least from just proximal of the proximal most marker band to just distal of the distal most marker band, the built-up layer having proximal and distal ends; and
- a stent having a proximal end and a distal end, the stent mounted coaxially upon the balloon, the built-up layer extending coaxially within the stent, the built-up layer not extending beyond the proximal and distal ends of the stent, and the built-up layer being sufficiently thick such that the balloon will not puncture when crimping the stent brings the balloon into contact with the marker band, with the built-up layer being sufficiently thick as to cause the balloon to expand evenly and the stent to deploy uniformly.

14. A catheter system according to claim 13 wherein the built-up layer is formed of at least one layer of heat shrinkable tubing.

15. A catheter system according to claim 14 wherein the length of the built up layer is approximately one-third of the length of the stent.

16. A catheter system according to claim 13 wherein the built-up layer is formed from molded adhesive.

17. A catheter system according to claim 16 wherein the inner lumen tube is coaxial with and extends longitudinally within the inflation lumen tube.

* * * * *

UNITED STATES PATENT AND TRADEMARK OFFICE
CERTIFICATE OF CORRECTION

PATENT NO. : 5,653,691
DATED : August 5, 1997
INVENTOR(S) : Rupp et al.

It is certified that error appears in the above-identified patent and that said Letters Patent is hereby corrected as shown below:

Col. 4, Line 65: "stem" should be "stent"

Signed and Sealed this

Tenth Day of November 1998

Attest:

BRUCE LEHMAN

*Attesting Officer*  *Commissioner of Patents and Trademarks*